US008465672B2

(12) United States Patent
Lietzau et al.

(10) Patent No.: US 8,465,672 B2
(45) Date of Patent: Jun. 18, 2013

(54) TETRAHYDROPYRAN COMPOUNDS

(75) Inventors: Lars Lietzau, Darmstadt (DE); Markus Czanta, Darmstadt (DE); Atsutaka Manabe, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 918 days.

(21) Appl. No.: 12/377,820

(22) PCT Filed: Jul. 17, 2007

(86) PCT No.: PCT/EP2007/006426
§ 371 (c)(1), (2), (4) Date: Feb. 17, 2009

(87) PCT Pub. No.: WO2008/019746
PCT Pub. Date: Feb. 21, 2008

(65) Prior Publication Data
US 2011/0253934 A1    Oct. 20, 2011

(30) Foreign Application Priority Data
Aug. 18, 2006 (DE) .......................... 10 2006 038 949

(51) Int. Cl.
*C09K 19/00* (2006.01)
*C09K 19/02* (2006.01)
*C09K 19/06* (2006.01)
*C09K 19/52* (2006.01)

(52) U.S. Cl.
USPC .............. 252/299.61; 252/299.01; 252/299.6; 252/299.62; 252/299.63; 252/299.64; 252/299.65; 252/299.66; 349/1; 349/56; 428/1.1; 428/1.3

(58) Field of Classification Search
USPC ........... 252/299.01, 299.6–66, 299.6–299.66; 430/20; 428/1.1, 1.3; 349/1, 56
See application file for complete search history.

(56) References Cited

U.S. PATENT DOCUMENTS

| | | | |
|---|---|---|---|
| 7,022,865 B2 * | 4/2006 | Goulding et al. | 549/428 |
| 7,344,761 B2 | 3/2008 | Kirsch | |
| 2005/0179007 A1 | 8/2005 | Manabe et al. | |
| 2005/0205842 A1 | 9/2005 | Heckmeier et al. | |
| 2006/0061699 A1 | 3/2006 | Kirsch et al. | |
| 2007/0034828 A1 | 2/2007 | Kirsch et al. | |
| 2007/0176144 A1 | 8/2007 | Francis et al. | |

FOREIGN PATENT DOCUMENTS

| | | |
|---|---|---|
| DE | 10 2004 056 901 A1 | 7/2005 |
| DE | 10 2004 058 002 A1 | 7/2005 |
| EP | 1 813 662 A1 | 8/2007 |
| EP | 1 842 894 A2 | 10/2007 |
| WO | WO 2004/048501 A1 | 6/2004 |
| WO | WO 2004/106459 A1 | 12/2004 |
| WO | WO 2005/081215 A1 | 9/2005 |

OTHER PUBLICATIONS

International Search Report of PCT/EP2007/006426 (Oct. 16, 2007).

* cited by examiner

*Primary Examiner* — Geraldina Visconti
(74) *Attorney, Agent, or Firm* — Millen, White, Zelano & Branigan, P.C.

(57) ABSTRACT

The invention relates to mesogenic tetrahydropyran compounds having at least four rings, of the formula I

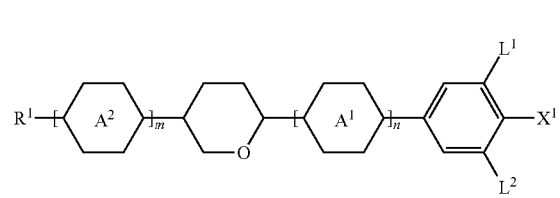

I in which $R^1$, $A^1$, $A^2$, $X^1$, $L^1$, $L^2$, m and n have the meanings indicated in Claim 1, and to a process for the preparation thereof, to the use thereof in liquid-crystalline media, to liquid-crystalline media comprising at least one compound of the formula I, and to electro-optical displays containing a liquid-crystalline medium of this type.

19 Claims, No Drawings

TETRAHYDROPYRAN COMPOUNDS

The present invention relates to compounds having a pyran ring, to a liquid-crystalline medium, to the use thereof for electro-optical purposes, and to displays containing this medium.

In the preceding years, the areas of application of liquid-crystalline compounds have been considerably broadened to various types of display device, electro-optical devices, electronic components, sensors, etc. For this reason, a number of different chemical structures have been proposed, in particular in the area of nematic liquid crystals. The nematic liquid-crystal mixtures have to date found the broadest application in flat display devices. They have been employed, in particular, in passive TN or STN matrix displays or systems having a TFT active matrix.

The liquid-crystalline compounds according to the invention can be used as component(s) of liquid-crystalline media, in particular for displays based on the principle of the twisted cell, the guest-host effect, the effect of deformation of aligned phases DAP or ECB (electrically controlled birefringence), the IPS (in-plane switching) effect or the effect of dynamic scattering.

Tetrahydropyran compounds as liquid-crystalline compounds are known, for example from the publications WO 2004/106459 and WO 2004/048501. The publication DE 102004058002 A1 discloses a tetracyclic compound of the formula

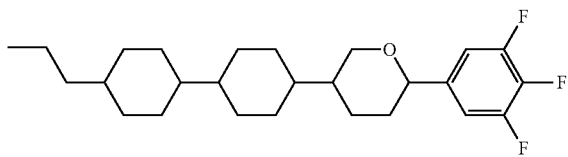

as constituent of a liquid-crystalline mixture.

The invention relates to mesogenic compounds of the formula I

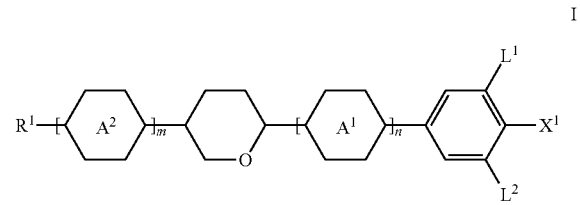

in which
$R^1$ and $X^1$ denote H, an unsubstituted or mono- or poly-halogen-substituted alkyl or alkoxy radical having 1 to 15 carbon atoms or alkenyl or alkenyloxy radical having 2 to 15 carbon atoms, where, in addition, one or more $CH_2$ groups in these radicals may each, independently of one another, be replaced by —C≡C—, —CH═CH—, —CF═CF—, —O—, —(CO)O— or —O(CO)— in such a way that O atoms are not linked directly to one another; or one of the radicals $R^1$ and $X^1$ also denotes F, Cl, CN, NCS, $SF_5$;
rings $A^1$ and $A^2$
denote 1,4-cyclohexylene, 1,4-cyclohexenylene or 1,4-cyclohexadienylene, which are unsubstituted or substituted by 1 to 3 F, preferably once,
$L^1$ and $L^2$, independently of one another, denote H or F;
m denotes 0 or 1; and
n denotes 1, 2 or 3;
where
m+n is ≧2.

The compounds accordingly have 4, 5 or 6 rings. $R^1$ and $X^1$ preferably do not simultaneously denote H.

The invention furthermore relates to the use of these compounds as components of liquid-crystalline media. The invention furthermore relates to a liquid-crystalline medium comprising at least two liquid-crystalline compounds, which is characterised in that it comprises at least one compound of the formula I according to the invention, and to liquid-crystal and electro-optical display elements which contain a liquid-crystalline medium according to the invention.

The compounds of the formula I can be used as components of liquid-crystalline media, in particular for displays based on the principle of the twisted cell, the guest-host effect, the effect of deformation of aligned phases or the effect of dynamic scattering.

One object of the invention was to find novel stable compounds which are suitable as component(s) of liquid-crystalline media, in particular for TN, STN, IPS and further active-matrix displays.

A further object of the present invention was to provide compounds which have a high dielectric anisotropy Δ∈, a high clearing point, a low optical anisotropy and a low rotational viscosity $γ_1$. In addition, the compounds according to the invention should be thermally and photochemically stable. Furthermore, the compounds according to the invention should be suitable for use in liquid-crystalline mixtures in that they can be dissolved in conventional mixtures and do not impair or improve the liquid-crystalline phase ranges thereof.

It has been found that the tetrahydropyran derivatives according to the invention are eminently suitable as components of liquid-crystalline media. They can be used to obtain stable, liquid-crystalline media, particularly suitable for TN-TFT, STN and IPS liquid-crystal displays. The compounds according to the invention are stable chemically, thermally and to (UV) light. They are colourless in the pure state. They are also distinguished by a positive dielectric anisotropy Δ∈, as a consequence of which lower threshold voltages are required on use in optical switching elements. In addition, the compounds have favourable, i.e. low, values of the rotational viscosity. Further advantages of the compounds according to the invention are the higher polarity of the tetrahydropyran ring compared with cyclohexane derivatives, with no harmful effect on the (electro)optical properties occurring.

Liquid-crystalline media having very low values of the optical anisotropy are of particular importance for reflective and transflective applications, i.e. applications in which the particular LCD experiences no or only supporting backlighting. In this connection, it is also possible to obtain liquid-crystalline mixtures according to the invention comprising the derivatives according to the invention having very low values of the optical anisotropy and slightly positive to highly positive values of the dielectric anisotropy.

The provision of the tetrahydropyran derivatives according to the invention very generally considerably broadens the range of compounds which are suitable, from various applicational points of view, for the preparation of liquid-crystalline mixtures.

In the mixture with suitable co-components, the compounds according to the invention form liquid-crystalline mesophases in a temperature range which is favourably located for electro-optical use. Liquid-crystalline media having broad nematic phase ranges can be prepared from the compounds according to the invention and further substances. The compounds according to the invention can be employed successfully since they are readily soluble in the conventional base mixtures.

The tetrahydropyran derivatives have a broad range of applications. Depending on the choice of substituents, these compounds can serve as base materials of which liquid-crystalline media are predominantly composed. However, it is also possible to add liquid-crystalline base materials from other classes of compound to the compounds according to the invention in order, for example, to modify the dielectric and/or optical anisotropy of a dielectric of this type and/or to optimise its threshold voltage and/or its viscosity.

It is preferred for $R^1$ in the compounds of the formula I according to the invention to represent a straight-chain alkyl or alkenyl radical, in particular a straight-chain and unsubstituted alkyl or alkenyl radical having 1, 2, 3, 4, 5, 6 or 7 or 2, 3, 4, 5, 6 or 7 carbon atoms respectively. Illustrative preferred radicals $R^1$ are, inter alia, methyl, ethyl, n-propyl, n-butyl, n-pentyl, n-hexyl, n-heptyl, vinyl, 1E-propenyl, 2-propenyl, 1E-butenyl, 3-butenyl, 1E-pentenyl, 3E-pentenyl, 1E-hexenyl and 1E-heptenyl. The substituent $R^1$ is therefore preferably a straight-chain alkyl or alkenyl radical having 1-6 or 2-6 C atoms respectively.

$X^1$ preferably denotes F, Cl, CN, NCS, $SF_5$, a halogenated alkyl radical, halogenated alkoxy radical, halogenated alkenyl radical or halogenated alkenyloxy radical, each having up to 7 C atoms.

$X^1$ particularly preferably denotes F, Cl, CN, $CF_3$, $CF_2H$, $OCF_3$, $OCF_2H$, $OCFHCF_3$, $OCFHCH_2F$, $OCFHC_2HF$, $OCF_2CH_3$, $OCF_2CH_2F$, $OCF_2CHF_2$, $OCF_2CF_2CF_2H$, $OCF_2CF_2CH_2F$, $OCFHCF_2CF_3$, $OCFHCF_2CHF_2$, $OCFHCFHCF_3$, $OCH_2CF_2CF_3$, $OCF_2CF_2CF_3$, $OCF_2CFHCHF_2$, $OCF_2CH_2CHF_2$, $OCFHCF_2CHF_2$, $OCFHCFHCHF_2$, $OCFHCH_2CF_3$, $OCH_2CFHCF_3$, $OCH_2CF_2CHF_2$, $OCF_2CFHCH_3$, $OCF_2CH_2CHF_2$, $OCFHCF_2CH_3$, $OCFHCFHCHF_2$, $OCFHCH_2CF_3$, $OCH_2CF_2CHF_2$, $OCH_2CFHCHF_2$, $OCF_2CH_2CH_3$, $OCFHCFHCH_3$, $OCFHCH_2CHF_2$, $OCH_2CF_2CH_3$, $OCH_2CFHCHF_2$, $OCH_2CH_2CHF_2$, $OCHCH_2CH_3$, $OCH_2CFHCH_3$, $OCH_2CH_2CHF_2$, $OCClFCF_3$, $OCClFCClF_2$, $OCClFCHF_2$, $OCFHCCl_2F$, $OCClFCHF_2$, $OCClFCClF_2$, $OCF_2CHCl_2$, $OCF_2CHCl_2$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CHF_2$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCHF_2$, $OCF_2CF_2CCl_2F$, $OCF_2CCl_2CHF_2$, $OCF_2CH_2CClF_2$, $OCClFCF_2CFH_2$, $OCFHCF_2CCl_2F$, $OCClFCFHCHF_2$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCHF_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCCIH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CClH_2$, $OCCl_2CFHCFH_2$, $OCH_2CClFCFCl_2$, $OCH_2CH_2CF_2H$, $OCClHCClHCF_2H$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, $CH=CF_2$, $OCH=CF_2$, $CF=CF_2$, $OCF=CF_2$, $CF=CHF$, $OCF=CHF$, $CH=CHF$, $OCH=CHF$, in particular F, Cl, CN, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$ or $CH=CHF_2$.

It is very particularly preferred for $X^1$ in the compounds of the formula I according to the invention to denote a group from F, Cl, $CF_3$, $OCF_3$, $OCHF_2$ or CN, in particular F or $OCF_3$.

The rings $A^1$ and $A^2$ are preferably 1,4-cyclohexylene or 1,4-cyclohexenylene, optionally substituted by a fluorine atom, in particular 1,4-cyclohexylene, which is particularly preferably unsubstituted.

The 1,4-cyclohexenylene group is preferably of the formula

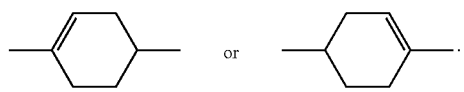

In the case where one of the rings $A^1$ and $A^2$ is substituted by a fluorine atom, it is preferably of the formula

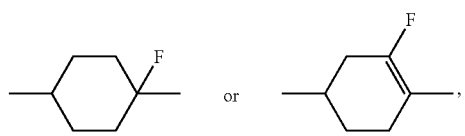

in particular of the latter formula.

The preferred values for m and n are m=0 and n=2 or m=1 and n=1. The sum of m and n is therefore preferably 2.

Preferred embodiments of the compounds of the formula I according to the invention are selected from compounds of the formulae I1 to I30:

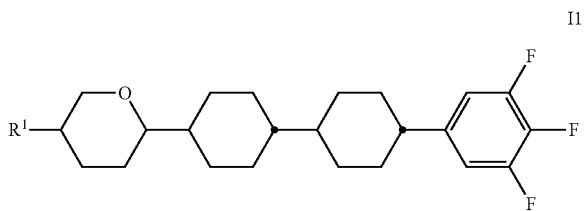

I1

I2

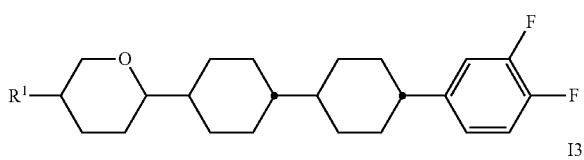

I3

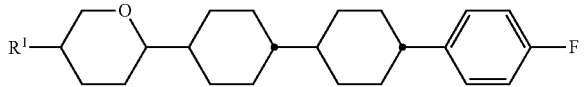

I4

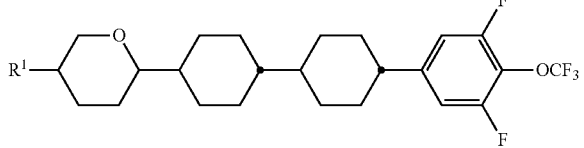

I5
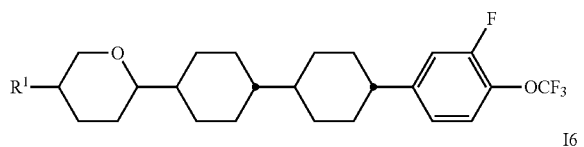
I6
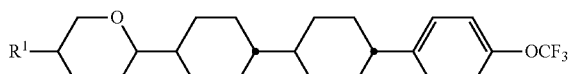
I7
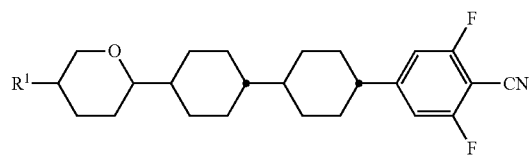
I8
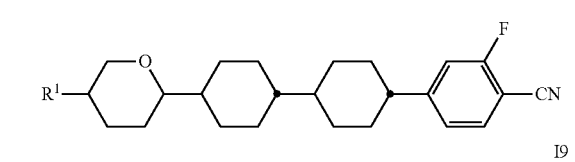
I9
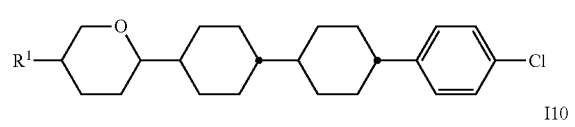
I10
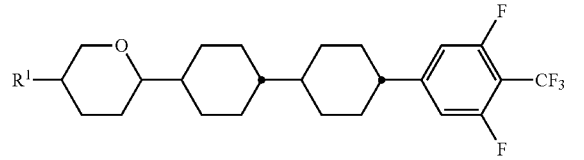
I11
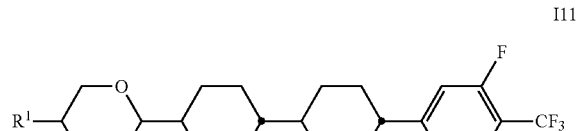
I12
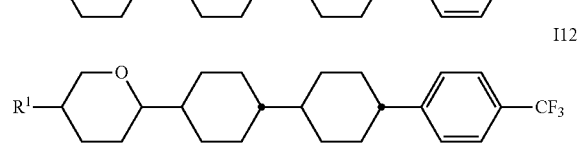
I13
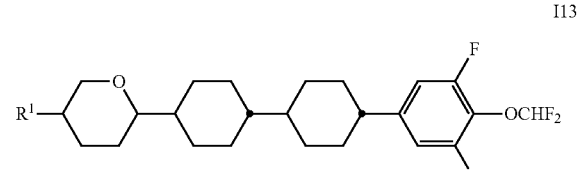
I14
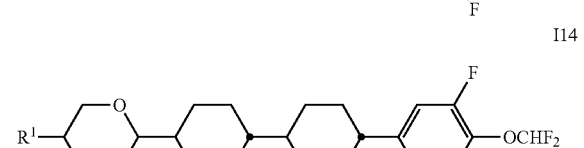
I15
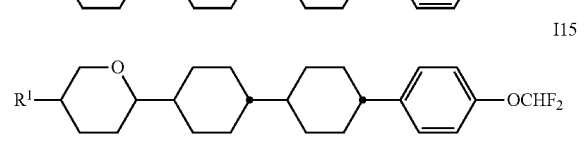
I16
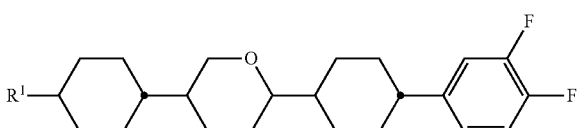
I17
I18
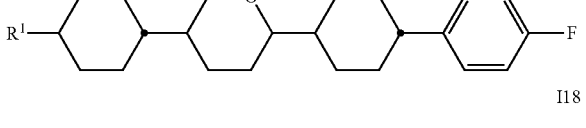
I19
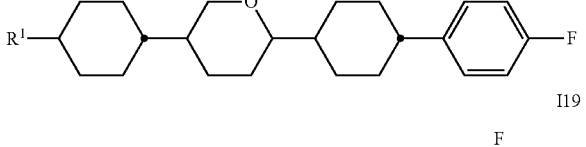
I20
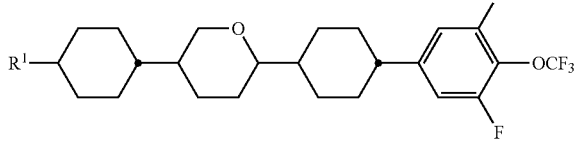
I21
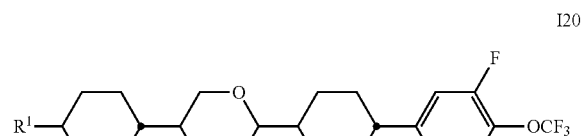
I22
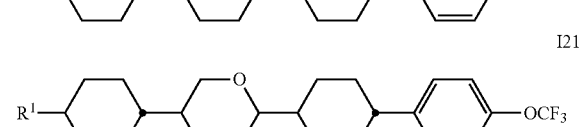
I23
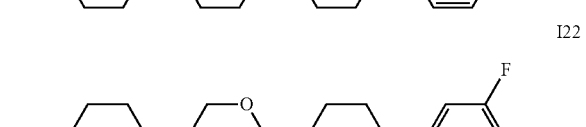
I24
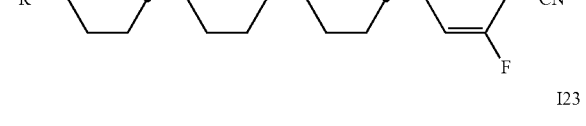
I25
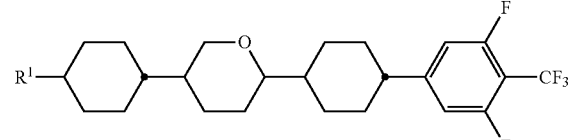

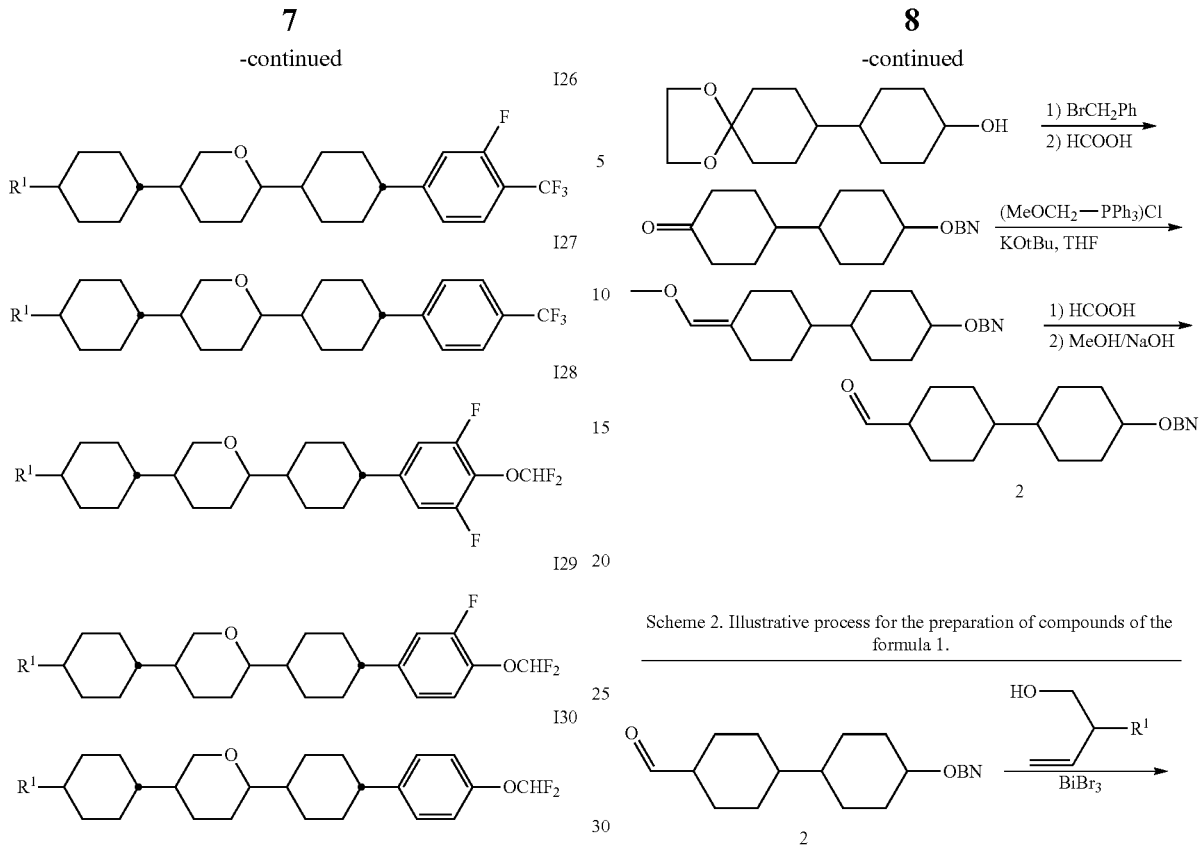

where R¹ is as defined above for formula I or preferably represents a straight-chain alkyl or alkenyl radical, in particular a straight-chain and un-substituted alkyl or alkenyl radical having 1 (only for alkyl), 2, 3, 4, 5, 6 or 7 carbon atoms. Particularly preferred compounds are the compounds of the formulae I1, I4, I16 and I19, in particular of the formulae I1 and I19.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail. The compounds of the formula I according to the invention are also accessible correspondingly by processes other than the process according to the invention.

Particularly suitable for the preparation are synthetic methods as shown in schemes 1, 2, 3, 4 and 5. Schemes 1 and 2 together represent a process for the preparation of the compounds of the formula I according to the invention where m=0 and n=2.

Scheme 1. Illustrative process for the preparation of an intermediate of the formula 2.

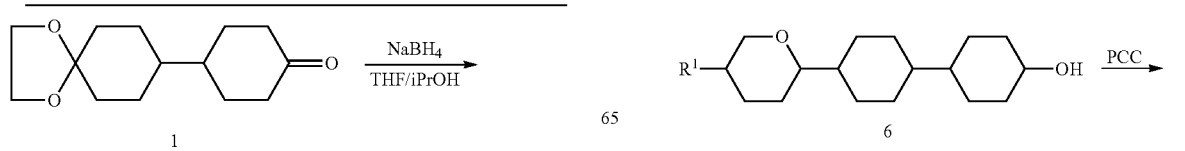

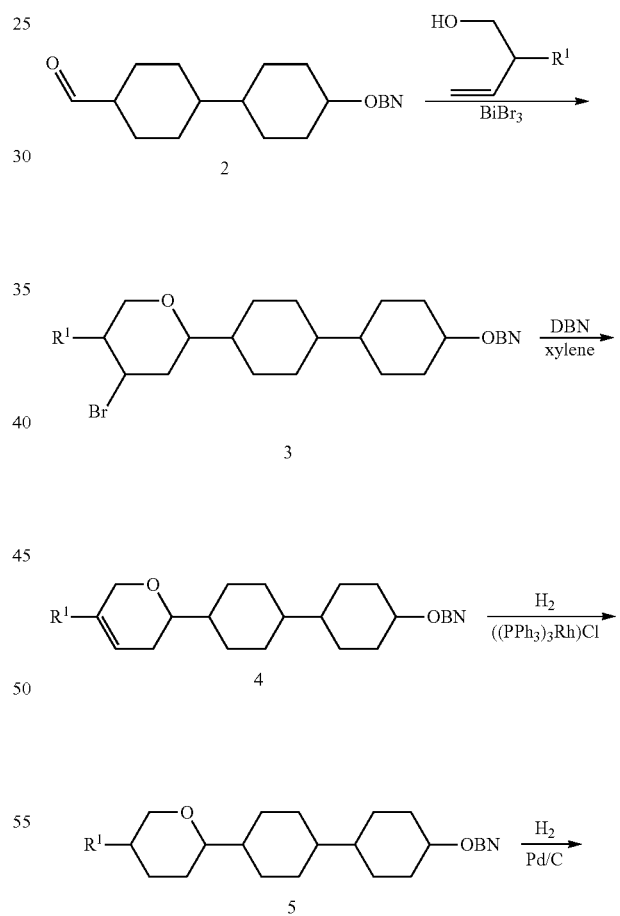

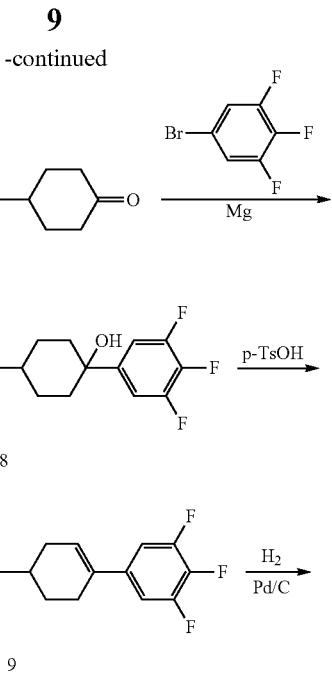

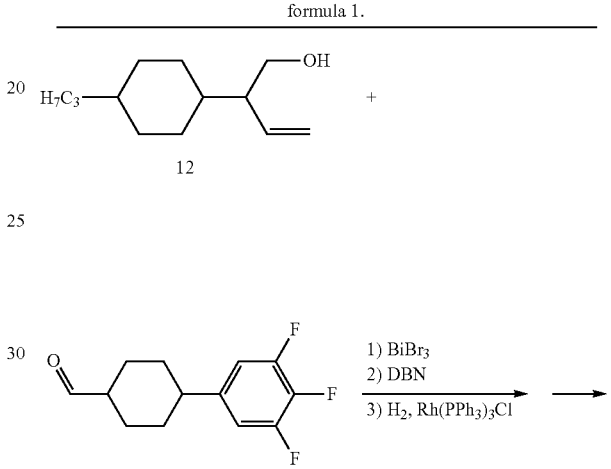

The benzyloxy group of compound 11 can be converted into an alkenyl group in the subsequent reaction steps in accordance with scheme 3 by cleaving off the benzyl radical reductively and oxidising the free hydroxyl group to the aldehyde (analogously to Example 1; reaction steps 1.4 and 1.5). An optionally substituted alkene is subsequently formed instead of the carbonyl group of the aldehyde by a Wittig-Horner reaction. Scheme 4 represents a process for the preparation of the compounds of the formula I where m=1 and n=1.

Scheme 4. Illustrative process for the preparation of compounds of the formula 1.

Unsaturated side chains are also introduced into the molecules via synthetic building block 11 (scheme 3).

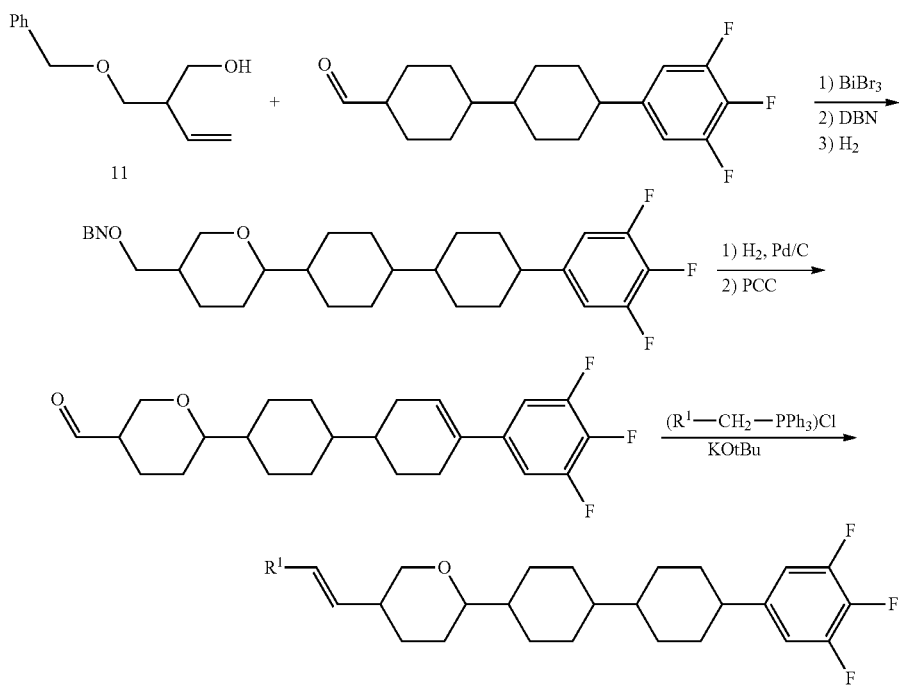

Scheme 3. Illustrative process for the preparation of compounds having alkenyl end groups.

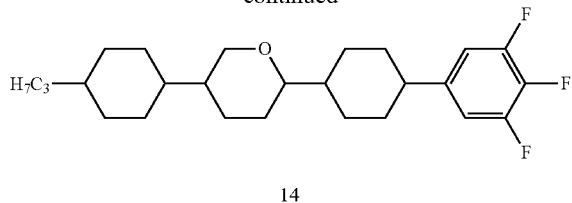

14

Unsaturated side chains are introduced into the molecules via synthetic building block 15:

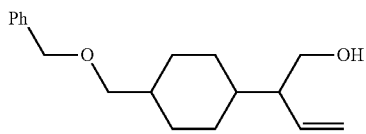

15

Synthetic building block 15 is a benzyloxy-substituted analogue of compound 12 (cf. scheme 4). After the reaction shown in scheme 4, the benzyloxy group can be converted into an alkenyl group in accordance with scheme 3.

A compound having the ring sequence of the formula 14 can also be prepared from suitable starting compounds via an addition reaction of an arylmetal compound (from 17) onto a correspondingly substituted tricyclic cyclohexanone of the formula 16 (scheme 5).

Scheme 5. Alternative preparation process to scheme 4.

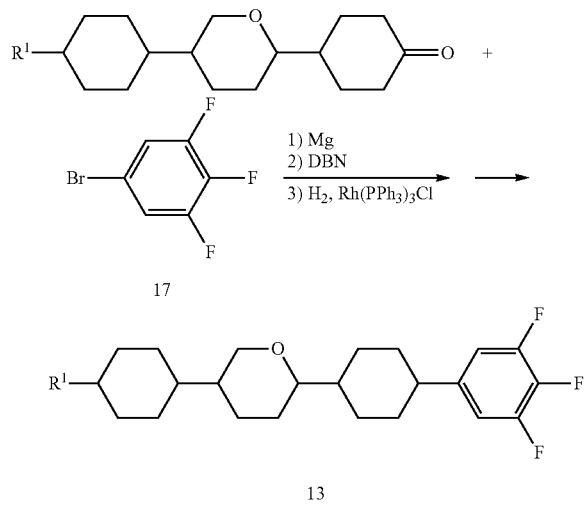

The invention also encompasses a process for the preparation of compounds of the formula I comprising a process step, which is characterised in that a cyclohexanone of the formula II

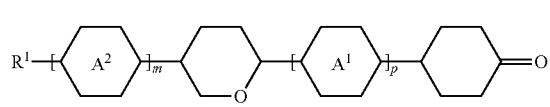

II in which
$R^1$, $A^1$, $A^2$ and m are as defined in formula I, and
p denotes 0, 1 or 2,
is reacted with an arylmetal compound of the formula III

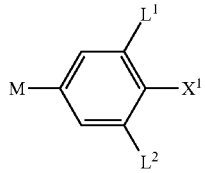

III in which
$L^1$, $L^2$ and $X^1$ are as defined in formula I, and
M denotes Li, MgCl or MgBr.

If radicals or substituents of the compounds according to the invention or the compounds according to the invention themselves can be in the form of optically active radicals, substituents or compounds since they have, for example, a centre of asymmetry, these are also encompassed by the present invention. It goes without saying here that the compounds of the formula I according to the invention can be in isomerically pure form, for example as pure enantiomers or diastereomers, or as a mixture of a plurality of isomers, for example as the racemate.

If $R^1$ in formula I does not denote H, the compounds of the formula I according to the invention can be in the form of cis- or trans-isomers, owing to the disubstitution of the pyran ring. In general, the respective trans-isomer is preferred for many uses. It can be obtained selectively, inter alia, by employing in the preparation process a precursor containing the pyran ring having the trans-configuration, which is itself obtained, for example, by isomerisation using base or acid, a preparation analogous to scheme 2, by recrystallisation and/or by chromatographic separation. These conventional processes can of course also be carried out with isomer mixtures of the final compounds of the formula I.

The invention also relates to liquid-crystalline media comprising one or more of the compounds of the formula I according to the invention. The liquid-crystalline media comprise at least two components. They are preferably obtained by mixing the components with one another. They are preferably based on a plurality of (preferably two, three or more) compounds of the formula I. The proportion of the compounds of the formula I is generally 1-95%, preferably 2-60% and particularly preferably in the range 5-30%. A process according to the invention for the preparation of a liquid-crystalline medium is therefore characterised in that at least one compound of the formula I is mixed with at least one further mesogenic compound, and additives are optionally added.

The achievable combinations of clearing point, viscosity at low temperature, thermal and UV stability and dielectric anisotropy are far superior to previous materials from the prior art.

The liquid-crystalline media according to the invention preferably comprise 2 to 40, particularly preferably 4 to 30, components as further constituents besides one or more compounds according to the invention. In particular, these media comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexanes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of the media according to the invention can be characterised by the formulae 1, 2, 3, 4 and 5:

$$R'\text{-L-E-}R'' \qquad 1$$

$$R'\text{-L-COO-E-}R'' \qquad 2$$

$$R'\text{-L-CF}_2\text{O-E-}R'' \qquad 3$$

$$R'\text{-L-CH}_2\text{CH}_2\text{-E-}R'' \qquad 4$$

$$R'\text{-L-C}{\equiv}\text{C-E-}R'' \qquad 5$$

In the formulae 1, 2, 3, 4 and 5, L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Py-, -G-Phe- and -G-Cyc- and their mirror images, where Phe denotes unsubstituted or fluorine-substituted 1,4-phenylene, Cyc denotes trans-1,4-cyclohexylene, Pyr denotes pyrimidine-2,5-diyl or pyridine-2,5-diyl, Dio denotes 1,3-dioxane-2,5-diyl, Py denotes tetrahydropyran-2,5-diyl and G denotes 2-(trans-1,4-cyclohexyl)ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe, Py and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

$R^1$ and/or $R''$ each, independently of one another, denote alkyl, alkenyl, alkoxy, alkoxyalkyl, alkenyloxy or alkanoyloxy having up to 8 C atoms, —F, —Cl, —CN, —NCS or —(O)$_i$CH$_{3-k}$F$_k$, where i is 0 or 1 and k is 1, 2 or 3.

In a smaller sub-group of the compounds of the formulae 1, 2, 3, 4 and 5, R' and R" each, independently of one another, denote alkyl, alkenyl, alkoxy, alkoxyalkyl, alkenyloxy or alkanoyloxy having up to 8 C atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is referred to as group B, R" denotes —F, —Cl, —NCS or —(O)$_i$CH$_{3-k}$F$_k$, where i is 0 or 1 and k is 1, 2 or 3. The compounds in which R" has this meaning are referred to by the sub-formulae 1b, 2b, 3b, 4b and 5b. Particular preference is given to those compounds of the sub-formulae 1b, 2b, 3b, 4b and 5b in which R" has the meaning —F, —Cl, —NCS, —CF$_3$, —OCHF$_2$ or —OCF$_3$.

In the compounds of the sub-formulae 1b, 2b, 3b, 4b and 5b, R' has the meanings indicated in the case of the compounds of the sub-formulae 1a to 5a and is preferably alkyl, alkenyl, alkoxy or alkoxyalkyl.

In a further smaller sub-group of the compounds of the formulae 1, 2, 3, 4 and 5, R" denotes —CN. This sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' has the meanings indicated in the case of the compounds of the sub-formulae 1a to 5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides compounds of the formula I according to the invention, the media according to the invention preferably comprise one or more compounds selected from groups A, B and/or C. The proportions by weight of the compounds from these groups in the media according to the invention are preferably:

group A: 0 to 90%, preferably 20 to 90%, particularly preferably 30 to 90%, group B: 0 to 80%, preferably 10 to 80%, particularly preferably 10 to 65%;

group C: 0 to 80%, preferably 0 to 80%, particularly preferably 0 to 50%;

where the sum of the proportions by weight of the group A, B and/or C compounds present in the respective media according to the invention is preferably 5 to 90% and particularly preferably 10 to 90%.

The liquid-crystal mixtures according to the invention are prepared in a manner which is conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multi-bottle" systems.

The dielectrics may also comprise further additives known to the person skilled in the art and described in the literature. For example, 0 to 15%, preferably 0 to 10%, of pleochroic dyes, chiral dopants, stabilisers or nanoparticles can be added. The individual compounds added are employed in concentrations of 0.01 to 6%, preferably 0.1 to 3%. However, the concentration data of the other constituents of the liquid-crystal mixtures, i.e. the liquid-crystalline or mesogenic compounds, are given here without taking into account the concentration of these additives.

The liquid-crystal mixtures according to the invention enable a significant broadening of the available parameter latitude.

The invention also relates to electro-optical displays (in particular TFT displays having two plane-parallel outer plates, which, together with a frame, form a cell, integrated non-linear elements for switching individual pixels on the outer plates, and a nematic liquid-crystal mixture having positive dielectric anisotropy and high specific resistance located in the cell) which contain media of this type, and to the use of these media for electro-optical purposes.

The term "alkyl" encompasses straight-chain and branched alkyl groups having 1-9 carbon atoms, in particular the straight-chain groups methyl, ethyl, propyl, butyl, pentyl, hexyl and heptyl. Groups having 2-5 carbon atoms are generally preferred.

The term "alkenyl" encompasses straight-chain and branched alkenyl groups having up to 9 carbon atoms, in particular the straight-chain groups. Particularly preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "halogenated alkyl radical" preferably encompasses mono- or polyfluorinated and/or -chlorinated radicals. Perhalogenated radicals are included. Particular preference is given to fluorinated alkyl radicals, in particular $CF_3$, $CH_2CF_3$, $CH_2CHF_2$, $CHF_2$, $CH_2F$, $CHFCF_3$ and $CF_2CHFCF_3$. The term "halogenated alkenyl radicals" and related terms are explained correspondingly.

The total amount of compounds of the formula I in the mixtures according to the invention is not crucial. The mixtures may therefore comprise one or more further components for the purposes of optimisation of various properties.

The construction of the matrix display according to the invention from polarisers, electrode base plates and surface-treated electrodes corresponds to the usual design for displays of this type. The term usual design is broadly drawn here and also encompasses all derivatives and modifications of the matrix display, in particular also matrix display elements based on poly-Si TFTs.

A significant difference between the displays according to the invention and the hitherto conventional ones based on the twisted nematic cell consists, however, in the choice of the liquid-crystal parameters of the liquid-crystal layer.

Further combinations of the embodiments and variations of the subject-matters of the invention are disclosed in the patent claims.

The following examples are intended to explain the invention without restricting it.

Above and below, percentage data denote percent by weight. All temperatures are indicated in degrees Celsius. Furthermore, C=crystalline state, N=nematic phase, Sm=smectic phase and I=isotropic phase. The data between these symbols represent the transition temperatures. $\Delta n$ denotes optical anisotropy (589 nm, 20° C.), $\Delta \in$ the dielectric anisotropy (1 kHz, 20° C.) and $\gamma_1$ the rotational viscosity (in the unit mPa·s).

The physical, physicochemical and electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

The dielectric anisotropy $\Delta \in$ of the individual substances is determined at 20° C. and 1 kHz. To this end, 5-10% by weight of the substance to be investigated are measured dissolved in the dielectrically positive mixture ZLI-4792 (Merck KGaA), and the measurement value is extrapolated to a concentration of 100%. The optical anisotropy $\Delta n$ is determined at 20° C. and a wavelength of 589.3 nm, the rotational viscosity $\gamma_1$ at 20° C., both likewise by linear extrapolation.

The following abbreviations are used in the examples and in the synthesis and reaction schemes:
DBN diazabicycloundecene
MTB ether methyl tert-butyl ether
OBN O-benzyl group
n-BuLi 1.6 molar solution of n-butyllithium in n-hexane
THF tetrahydrofuran
p-TsOH p-toluenesulfonic acid
RT room temperature
Pd/C palladium on active carbon (5%), containing water
KOtBu potassium tert-butoxide

EXAMPLE 1

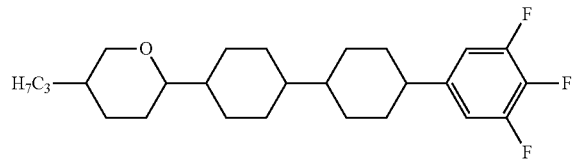

Reaction Step 1.1

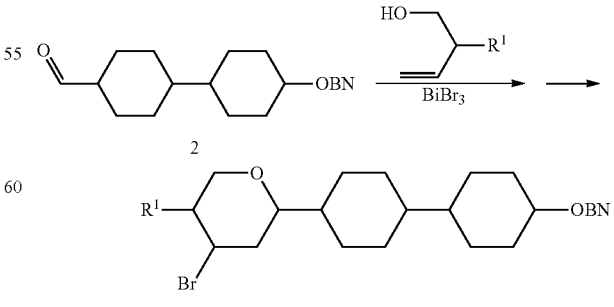

30.0 g (100 mmol) of the aldehyde 2 and 19.0 g (60%; 100 mmol) of 2-vinylpropanol are dissolved in 140 ml of dichloromethane, and 22.9 g (50 mmol) of bismuth(III) bromide are added. The batch is stirred overnight at RT. The batch is subsequently filtered through silica gel and evaporated. The bromine compound 3 is isolated.

Reaction Step 1.2

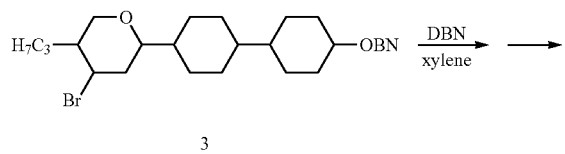

Under nitrogen, 53 g (111 mmol) of the bromine compound 3 are dissolved in 90 ml of toluene, 20 ml of DBN are added, and the mixture is heated at the boil for 8 h. 400 ml of water are subsequently added to the cooled batch, which is acidified using dilute sulfuric acid. The organic phase is separated off, washed with sodium hydrogencarbonate solution and evaporated. The residue obtained is passed over silica gel (toluene). Compound 4 is isolated.

Reaction Step 1.3

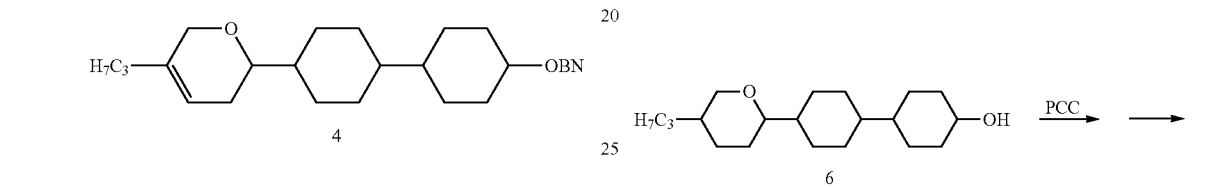

27 g (68 mmol) of the dihydropyran 4 are dissolved in 280 ml of methanol and 80 ml of toluene and hydrogenated at 8 bar/80° C. by means of (PPh$_3$)$_3$RhCl catalyst (1%) until the end of hydrogen uptake. The hydrogenation solution is evaporated, and the residue is passed over silica gel (toluene/MTB ether 9:1).

Reaction Step 1.4

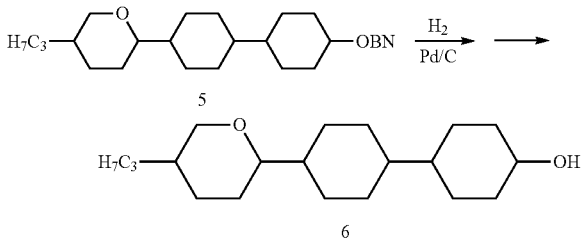

23.5 g (59 mmol) of the benzyl ether 5 are dissolved in 250 ml of THF and hydrogenated on a palladium catalyst. The catalyst is subsequently separated off, and the solution is evaporated. The residue obtained is employed in the following step without further purification.

Reaction Step 1.5

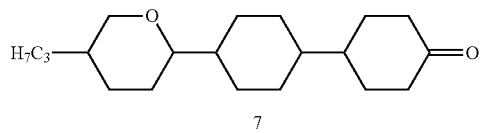

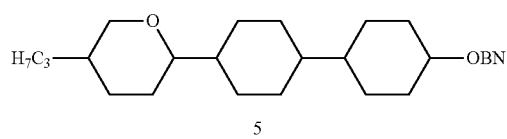

Under nitrogen, firstly 102 g (470 mmol) of pyridinium chlorochromate (PCC) and subsequently 138.6 g (449 mmol) of the alcohol 6 are added to a suspension of 200 g of kieselguhr in 2.5 l of dichloromethane. The suspension is stirred at RT for 16 h and filtered through Celite with suction. The filtrate is evaporated, and the residue is passed over silica gel (toluene/MTB ether 9:1).

Reaction Step 1.6

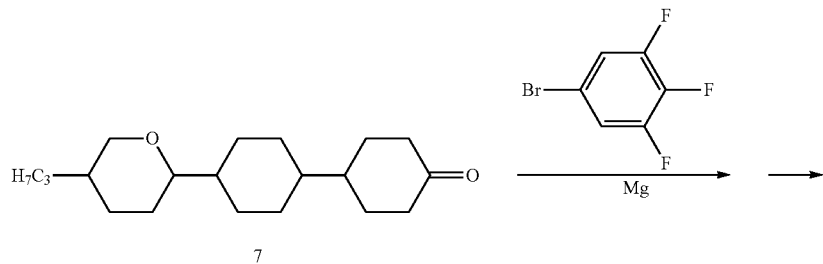

9.3 ml (78 mmol) of trifluorobromobenzene, dissolved in 30 ml of THF, are added to 1.9 g (78 mmol) of magnesium, and the corresponding Grignard compound is prepared. A solution of the ketone 7 in 30 ml of THF is added at the boiling point, and the mixture is refluxed for 1 h. The batch is subsequently hydrolysed using water, adjusted to pH 1 using hydrochloric acid, and 200 ml of MTB ether are added. The organic phase is evaporated, and the product is reacted in the next step without further purification.

Reaction Step 1.7

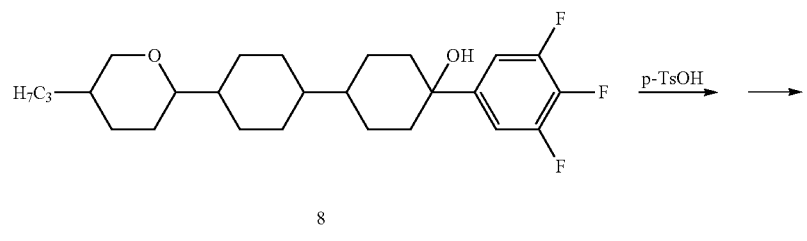

300 ml of xylene and 500 mg of p-toluenesulfonic acid are added to the alcohol 8 (about 20 mmol), and the mixture is refluxed on a water separator for 30 min. The batch is subsequently passed over silica gel (toluene) and evaporated. The residue is reacted without further purification.

Reaction Step 1.8

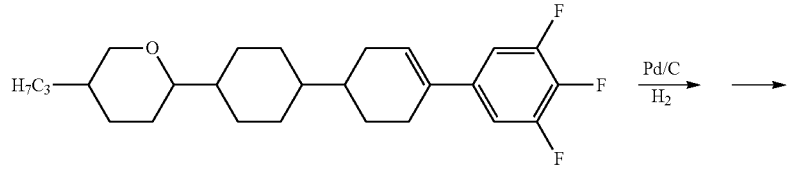

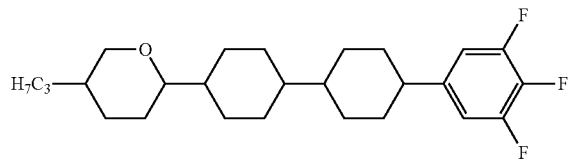

The cyclohexene compound 9 (4.9 g; 12 mmol) is dissolved in 50 ml of THF and hydrogenated on a palladium catalyst. The hydrogenation solution is evaporated, and the residue is passed over silica gel and subsequently crystallised from heptane.

C 95 SmB 169 N 246 I
Δε 14
Δn 0.106

The following compounds of the formula

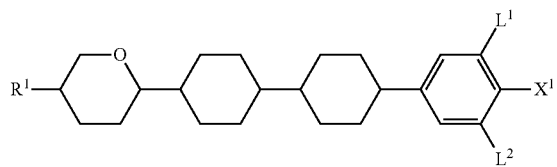

are prepared analogously to reaction steps 1.1 to 1.8:

| $R^1$ | $X^1$ | $L^1$ | $L^2$ | Values |
|---|---|---|---|---|
| H | F | H | H | |
| $CH_3$ | F | H | H | |
| $C_2H_5$ | F | H | H | |
| n-$C_3H_7$ | F | H | H | C 77 SmB 253 N 304 I; Δε 7.0; Δn 0.113 |
| n-$C_4H_9$ | F | H | H | |
| n-$C_5H_{11}$ | F | H | H | |
| n-$C_6H_{13}$ | F | H | H | |
| H | F | F | H | |
| $CH_3$ | F | F | H | |
| $C_2H_5$ | F | F | H | |
| n-$C_3H_7$ | F | F | H | C 35 SmB 215 N 278 I; Δε 10; Δn 0.107 |
| n-$C_4H_9$ | F | F | H | |
| n-$C_5H_{11}$ | F | F | H | |
| n-$C_6H_{13}$ | F | F | H | |
| H | F | F | F | |
| $CH_3$ | F | F | F | |
| $C_2H_5$ | F | F | F | |
| n-$C_3H_7$ | F | F | F | (cf. Example 1) |
| n$C_4H_9$ | F | F | F | |
| n-$C_5H_{11}$ | F | F | F | |
| n-$C_6H_{13}$ | F | F | F | |
| H | $OCF_3$ | H | H | |
| $CH_3$ | $OCF_3$ | H | H | |
| $C_2H_5$ | $OCF_3$ | H | H | |
| n-$C_3H_7$ | $OCF_3$ | H | H | |
| n-$C_4H_9$ | $OCF_3$ | H | H | |
| n-$C_5H_{11}$ | $OCF_3$ | H | H | |
| n-$C_6H_{13}$ | $OCF_3$ | H | H | |
| H | $OCF_3$ | F | H | |
| $CH_3$ | $OCF_3$ | F | H | |
| $C_2H_5$ | $OCF_3$ | F | H | |
| n-$C_3H_7$ | $OCF_3$ | F | H | |
| n-$C_4H_9$ | $OCF_3$ | F | H | |
| n-$C_5H_{11}$ | $OCF_3$ | F | H | |
| n-$C_6H_{13}$ | $OCF_3$ | F | H | |
| H | $OCF_3$ | F | F | |
| $CH_3$ | $OCF_3$ | F | F | |
| $C_2H_5$ | $OCF_3$ | F | F | |
| n-$C_3H_7$ | $OCF_3$ | F | F | C 78 SmB(C) 147 SmB(H) 167 N 264 I; Δε 15; Δn 0.104 |
| n$C_4H_9$ | $OCF_3$ | F | F | |
| n-$C_5H_{11}$ | $OCF_3$ | F | F | |
| n-$C_6H_{13}$ | $OCF_3$ | F | F | |
| H | CN | H | H | |
| $CH_3$ | CN | H | H | |
| $C_2H_5$ | CN | H | H | |
| n-$C_3H_7$ | CN | H | H | |
| n-$C_4H_9$ | CN | H | H | |
| n-$C_5H_{11}$ | CN | H | H | |
| n-$C_6H_{13}$ | CN | H | H | |
| H | CN | F | H | |
| $CH_3$ | CN | F | H | |
| $C_2H_5$ | CN | F | H | |
| n-$C_3H_7$ | CN | F | H | |
| n-$C_4H_9$ | CN | F | H | |
| n-$C_5H_{11}$ | CN | F | H | |
| n-$C_6H_{13}$ | CN | F | H | |
| H | CN | F | F | |
| $CH_3$ | CN | F | F | |
| $C_2H_5$ | CN | F | F | |
| n-$C_3H_7$ | CN | F | F | |
| n$C_4H_9$ | CN | F | F | |
| n-$C_5H_{11}$ | CN | F | F | |
| n-$C_6H_{13}$ | CN | F | F | |
| H | $OCHF_2$ | H | H | |
| $CH_3$ | $OCHF_2$ | H | H | |
| $C_2H_5$ | $OCHF_2$ | H | H | |
| n-$C_3H_7$ | $OCHF_2$ | H | H | |
| n-$C_4H_9$ | $OCHF_2$ | H | H | |

-continued

| R$^1$ | X$^1$ | L$^1$ | L$^2$ | Values |
|---|---|---|---|---|
| n-C$_5$H$_{11}$ | OCHF$_2$ | H | H | |
| n-C$_6$H$_{13}$ | OCHF$_2$ | H | H | |
| H | OCHF$_2$ | F | H | |
| CH$_3$ | OCHF$_2$ | F | H | |
| C$_2$H$_5$ | OCHF$_2$ | F | H | |
| n-C$_3$H$_7$ | OCHF$_2$ | F | H | |
| n-C$_4$H$_9$ | OCHF$_2$ | F | H | |
| n-C$_5$H$_{11}$ | OCHF$_2$ | F | H | |
| n-C$_6$H$_{13}$ | OCHF$_2$ | F | H | |
| H | OCHF$_2$ | F | F | |
| CH$_3$ | OCHF$_2$ | F | F | |
| C$_2$H$_5$ | OCHF$_2$ | F | F | |
| n-C$_3$H$_7$ | OCHF$_2$ | F | F | |
| nC$_4$H$_9$ | OCHF$_2$ | F | F | |
| n-C$_5$H$_{11}$ | OCHF$_2$ | F | F | |
| n-C$_6$H$_{13}$ | OCHF$_2$ | F | F | |
| H | CF$_3$ | H | H | |
| CH$_3$ | CF$_3$ | H | H | |
| C$_2$H$_5$ | CF$_3$ | H | H | |
| n-C$_3$H$_7$ | CF$_3$ | H | H | |
| n-C$_4$H$_9$ | CF$_3$ | H | H | |
| n-C$_5$H$_{11}$ | CF$_3$ | H | H | |
| n-C$_6$H$_{13}$ | CF$_3$ | H | H | |
| H | CF$_3$ | F | H | |
| CH$_3$ | CF$_3$ | F | H | |
| C$_2$H$_5$ | CF$_3$ | F | H | |
| n-C$_3$H$_7$ | CF$_3$ | F | H | |
| n-C$_4$H$_9$ | CF$_3$ | F | H | |
| n-C$_5$H$_{11}$ | CF$_3$ | F | H | |
| n-C$_6$H$_{13}$ | CF$_3$ | F | H | |
| H | CF$_3$ | F | F | |
| CH$_3$ | CF$_3$ | F | F | |
| C$_2$H$_5$ | CF$_3$ | F | F | |
| n-C$_3$H$_7$ | CF$_3$ | F | F | |
| nC$_4$H$_9$ | CF$_3$ | F | F | |
| n-C$_5$H$_{11}$ | CF$_3$ | F | F | |
| n-C$_6$H$_{13}$ | CF$_3$ | F | F | |
| H | CH$_3$ | F | F | |
| CH$_3$ | CH$_3$ | F | F | |
| C$_2$H$_5$ | CH$_3$ | F | F | |
| n-C$_3$H$_7$ | CH$_3$ | F | F | C 72 SmB(C) (−12) SmB(H) 259 N 280 I; Δε 4.6; Δn 0.113 |
| nC$_4$H$_9$ | CH$_3$ | F | F | |
| n-C$_5$H$_{11}$ | CH$_3$ | F | F | |
| n-C$_6$H$_{13}$ | CH$_3$ | F | F | |
| H | CH$_3$ | F | H | |
| CH$_3$ | CH$_3$ | F | H | |
| C$_2$H$_5$ | CH$_3$ | F | H | |
| n-C$_3$H$_7$ | CH$_3$ | F | H | C 63 SmB 276 N 301 I; Δε 2.8; Δn 0.124 |
| nC$_4$H$_9$ | CH$_3$ | F | H | |
| n-C$_5$H$_{11}$ | CH$_3$ | F | H | |
| n-C$_6$H$_{13}$ | CH$_3$ | F | H | |
| H | CH$_3$ | H | H | |
| CH$_3$ | CH$_3$ | H | H | |
| C$_2$H$_5$ | CH$_3$ | H | H | |
| n-C$_3$H$_7$ | CH$_3$ | H | H | |
| nC$_4$H$_9$ | CH$_3$ | H | H | |
| n-C$_5$H$_{11}$ | CH$_3$ | H | H | |
| n-C$_6$H$_{13}$ | CH$_3$ | H | H | |

EXAMPLE 2

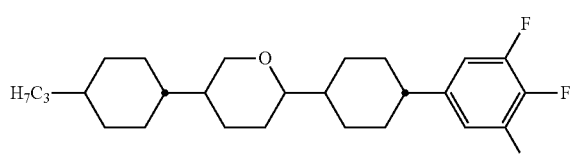

Reaction Step 2.1

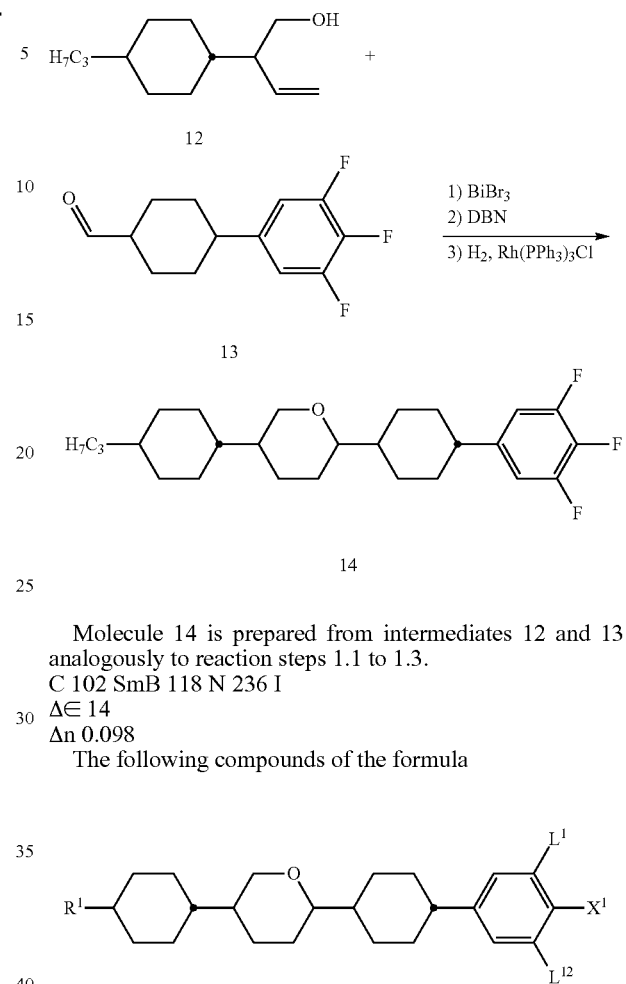

Molecule 14 is prepared from intermediates 12 and 13 analogously to reaction steps 1.1 to 1.3.
C 102 SmB 118 N 236 I
Δε 14
Δn 0.098

The following compounds of the formula are prepared analogously to reaction step 2.1:

| R$^1$ | X$^1$ | L$^1$ | L$^2$ | Values |
|---|---|---|---|---|
| H | F | H | H | |
| CH$_3$ | F | H | H | |
| C$_2$H$_5$ | F | H | H | |
| n-C$_3$H$_7$ | F | H | H | |
| n-C$_4$H$_9$ | F | H | H | |
| n-C$_5$H$_{11}$ | F | H | H | |
| n-C$_6$H$_{13}$ | F | H | H | |
| H | F | F | H | |
| CH$_3$ | F | F | H | |
| C$_2$H$_5$ | F | F | H | |
| n-C$_3$H$_7$ | F | F | H | |
| n-C$_4$H$_9$ | F | F | H | |
| n-C$_5$H$_{11}$ | F | F | H | |
| n-C$_6$H$_{13}$ | F | F | H | |
| H | F | F | F | |
| CH$_3$ | F | F | F | |
| C$_2$H$_5$ | F | F | F | |
| n-C$_3$H$_7$ | F | F | F | (cf. Example 2) |
| nC$_4$H$_9$ | F | F | F | |
| n-C$_5$H$_{11}$ | F | F | F | |
| n-C$_6$H$_{13}$ | F | F | F | |
| H | OCF$_3$ | H | H | |
| CH$_3$ | OCF$_3$ | H | H | |
| C$_2$H$_5$ | OCF$_3$ | H | H | |
| n-C$_3$H$_7$ | OCF$_3$ | H | H | |
| n-C$_4$H$_9$ | OCF$_3$ | H | H | |

-continued

| R¹ | X¹ | L¹ | L² | Values |
|---|---|---|---|---|
| n-C₅H₁₁ | OCF₃ | H | H | |
| n-C₆H₁₃ | OCF₃ | H | H | |
| H | OCF₃ | F | H | |
| CH₃ | OCF₃ | F | H | |
| C₂H₅ | OCF₃ | F | H | |
| n-C₃H₇ | OCF₃ | F | H | |
| n-C₄H₉ | OCF₃ | F | H | |
| n-C₅H₁₁ | OCF₃ | F | H | |
| n-C₆H₁₃ | OCF₃ | F | H | |
| H | OCF₃ | F | F | |
| CH₃ | OCF₃ | F | F | |
| C₂H₅ | OCF₃ | F | F | |
| n-C₃H₇ | OCF₃ | F | F | |
| nC₄H₉ | OCF₃ | F | F | |
| n-C₅H₁₁ | OCF₃ | F | F | |
| n-C₆H₁₃ | OCF₃ | F | F | |
| H | CN | H | H | |
| CH₃ | CN | H | H | |
| C₂H₅ | CN | H | H | |
| n-C₃H₇ | CN | H | H | |
| n-C₄H₉ | CN | H | H | |
| n-C₅H₁₁ | CN | H | H | |
| n-C₆H₁₃ | CN | H | H | |
| H | CN | F | H | |
| CH₃ | CN | F | H | |
| C₂H₅ | CN | F | H | |
| n-C₃H₇ | CN | F | H | |
| n-C₄H₉ | CN | F | H | |
| n-C₅H₁₁ | CN | F | H | |
| n-C₆H₁₃ | CN | F | H | |
| H | CN | F | F | |
| CH₃ | CN | F | F | |
| C₂H₅ | CN | F | F | |
| n-C₃H₇ | CN | F | F | |
| nC₄H₉ | CN | F | F | |
| n-C₅H₁₁ | CN | F | F | |
| n-C₆H₁₃ | CN | F | F | |
| H | OCHF₂ | H | H | |
| CH₃ | OCHF₂ | H | H | |
| C₂H₅ | OCHF₂ | H | H | |
| n-C₃H₇ | OCHF₂ | H | H | |
| n-C₄H₉ | OCHF₂ | H | H | |
| n-C₅H₁₁ | OCHF₂ | H | H | |
| n-C₆H₁₃ | OCHF₂ | H | H | |
| H | OCHF₂ | F | H | |
| CH₃ | OCHF₂ | F | H | |
| C₂H₅ | OCHF₂ | F | H | |
| n-C₃H₇ | OCHF₂ | F | H | |
| n-C₄H₉ | OCHF₂ | F | H | |
| n-C₅H₁₁ | OCHF₂ | F | H | |
| n-C₆H₁₃ | OCHF₂ | F | H | |
| H | OCHF₂ | F | F | |
| CH₃ | OCHF₂ | F | F | |
| C₂H₅ | OCHF₂ | F | F | |
| n-C₃H₇ | OCHF₂ | F | F | |
| nC₄H₉ | OCHF₂ | F | F | |
| n-C₅H₁₁ | OCHF₂ | F | F | |
| n-C₆H₁₃ | OCHF₂ | F | F | |
| H | CF₃ | H | H | |
| CH₃ | CF₃ | H | H | |
| C₂H₅ | CF₃ | H | H | |
| n-C₃H₇ | CF₃ | H | H | |
| n-C₄H₉ | CF₃ | H | H | |
| n-C₅H₁₁ | CF₃ | H | H | |
| n-C₆H₁₃ | CF₃ | H | H | |
| H | CF₃ | F | H | |
| CH₃ | CF₃ | F | H | |
| C₂H₅ | CF₃ | F | H | |
| n-C₃H₇ | CF₃ | F | H | |
| n-C₄H₉ | CF₃ | F | H | |
| n-C₅H₁₁ | CF₃ | F | H | |
| n-C₆H₁₃ | CF₃ | F | H | |
| H | CF₃ | F | F | |
| CH₃ | CF₃ | F | F | |
| C₂H₅ | CF₃ | F | F | |
| n-C₃H₇ | CF₃ | F | F | |
| nC₄H₉ | CF₃ | F | F | |
| n-C₅H₁₁ | CF₃ | F | F | |
| n-C₆H₁₃ | CF₃ | F | F | |

The invention claimed is:

1. A tetrahydropyran compound of formula I

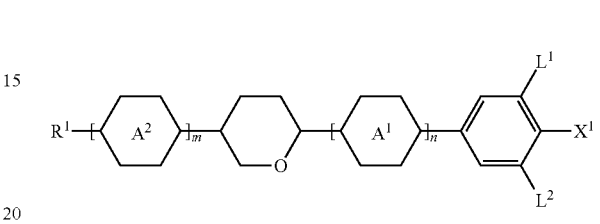

in which
R¹ and X¹ denote H, an unsubstituted or mono- or poly-halogen-sub-stituted alkyl or alkoxy radical having 1 to 15 carbon atoms or alkenyl or alkenyloxy radical having 2 to 15 carbon atoms, in which one or more CH₂ groups are optionally each, independently of one another, replaced by —C≡C—, —CH═CH—, —CF═CF—, —O—, —(CO)O— or —O(CO)— in such a way that O atoms are not linked directly to one another; or one of the radicals R¹ and X¹ also denotes F, Cl, CN, NCS or SF₅,
rings A¹ and A² denote, independently of one another, 1,4-cyclohexylene, 1,4-cyclohexenylene or 1,4-cyclohexadienylene, which are unsubstituted or substituted by 1 to 3 F,
L¹ and L² denote, independently of one another, H or F,
m denotes 0 or 1 and
n denotes 1, 2 or 3,
where m+n is ≧2.

2. A compound according to claim 1, wherein rings A¹ and A², independently of one another, denote 1,4-cyclohexylene or 1,4-cyclohexenylene.

3. A compound according to claim 1, wherein n denotes 1.

4. A compound according to claim 1, wherein R¹ denotes alkyl, alkoxy, alkenyl or alkenyloxy having up to 8 carbon atoms.

5. A compound according to claim 1, wherein X¹ denotes F, Cl, CN, NCS, SF₅, a halogenated alkyl radical, halogenated alkoxy radical, halogenated alkenyl radical or halogenated alkenyloxy radical, each having up to 7 C atoms.

6. A compound according to claim 1, wherein L¹ denotes fluorine and L² denotes fluorine or hydrogen.

7. A compound according to claim 1, wherein L¹ and L² denote fluorine.

8. A compound according to claim 1, which is one of formulae I1 to I30

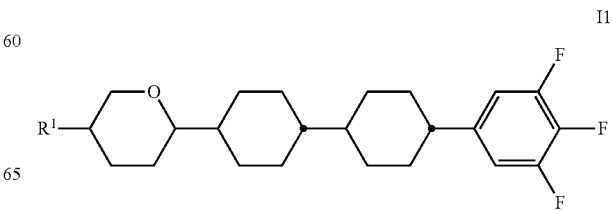

I2
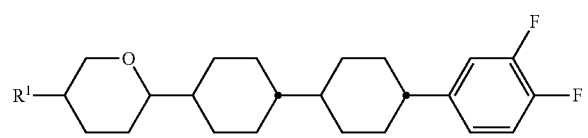
I3
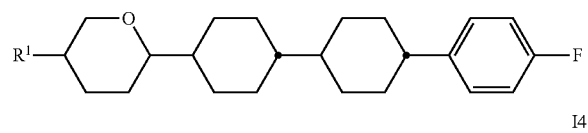
I4
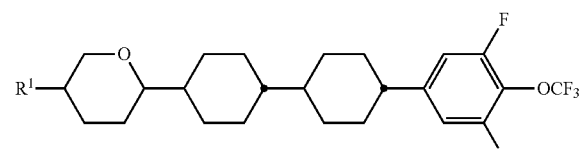
I5
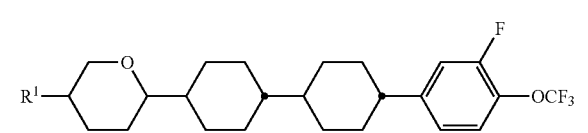
I6
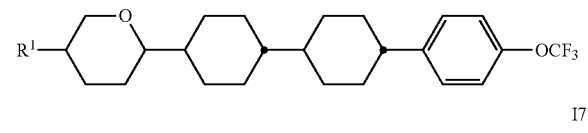
I7
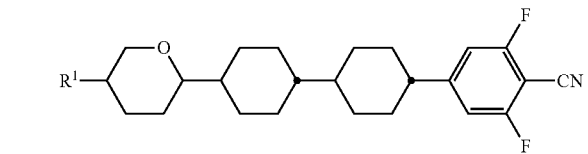
I8
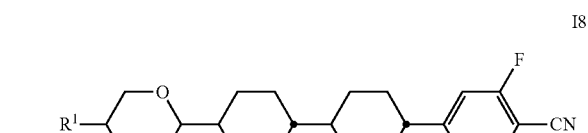
I9
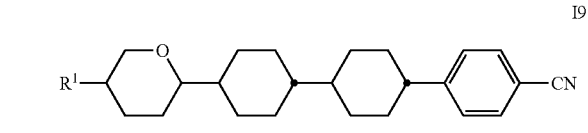
I10
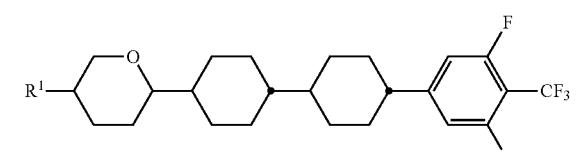
I11
I12
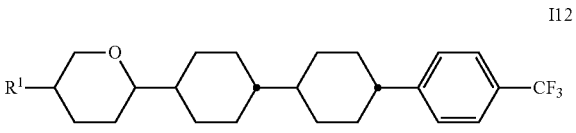
I13
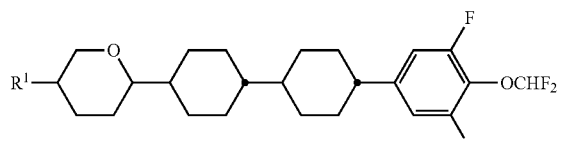
I14
I15
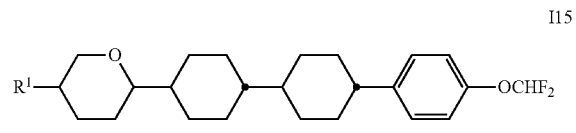
I16
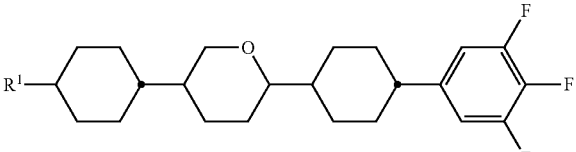
I17
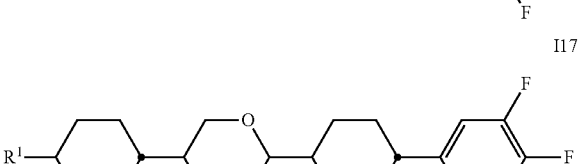
I18
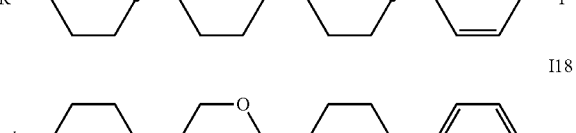
I19
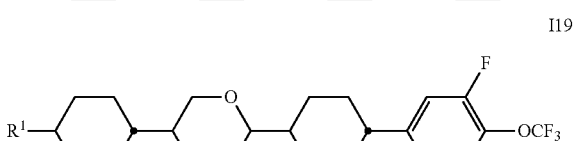
I20
I21
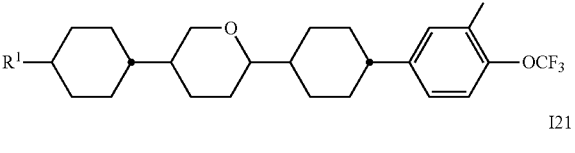

-continued

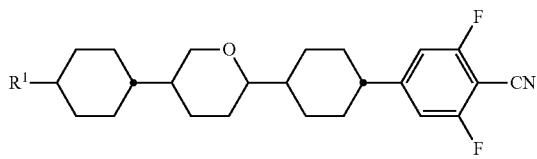
I22

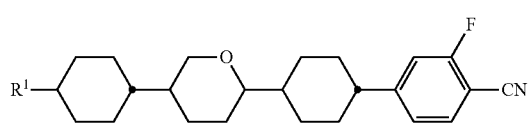
I23

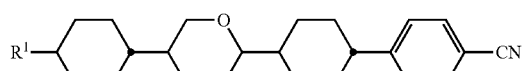
I24

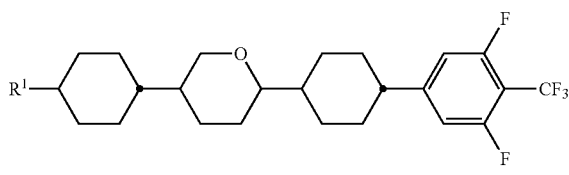
I25

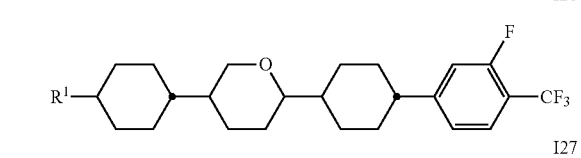
I26

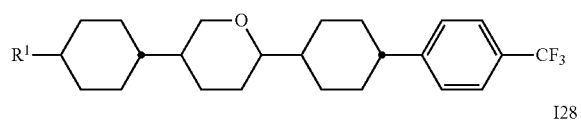
I27

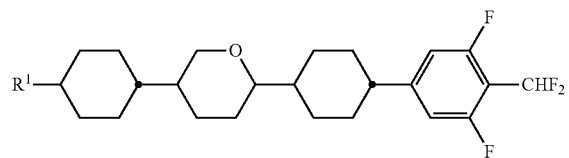
I28

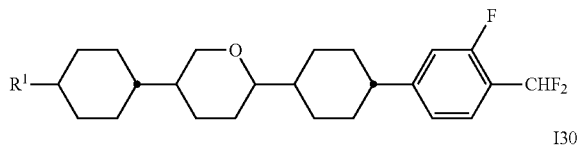
I29

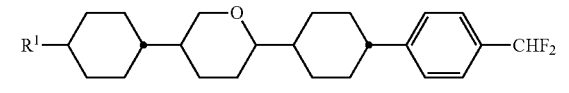
I30 where $R^1$ denotes H, F, Cl, CN, NCS or $SF_5$, or an unsubstituted or mono- or poly- halogen-substituted alkyl or alkoxy radical having 1 to 15 carbon atoms or alkenyl or alkenyloxy radical having 2 to 15 carbon atoms, in which one or more $CH_2$ groups are optionally each, independently of one another, replaced by —C≡C—, —CH=CH—, —CF=CF—, —O—, —(CO)O— or —O(CO)—in such a way that O atoms are not linked directly to one another.

9. A compound according to claim 1, wherein the substituents on the tetrahydropyran ring in the 1,4-position are in the trans-position to one another.

10. A process for preparing a compound according to claim 1, comprising reacting a cyclohexanone of formula II

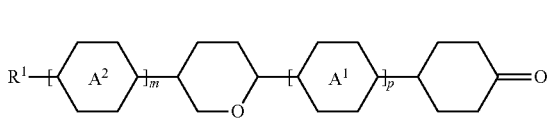
II in which $R^1$, $A^1$, $A^2$ and m are as defined in formula I, and p denotes 0, 1 or 2, with an arylmetal compound of formula III

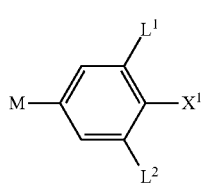
III in which $L^1$, $L^2$ and $X^1$ are as defined in formula I, and

M denotes Li, MgCl or MgBr.

11. A liquid-crystalline medium, comprising at least two mesogenic compounds, which comprises at least one compound of formula I according to claim 1.

12. An electro-optical device, containing a liquid-crystalline medium according to claim 11.

13. An electro-optical liquid-crystal display, containing a liquid-crystalline medium according to claim 11.

14. A method of generating an electro-optical effect comprising applying a voltage to a display according to claim 13.

15. A method of generating an electro-optical effect comprising applying a voltage to a device according to claim 12.

16. A compound according to claim 1, which is

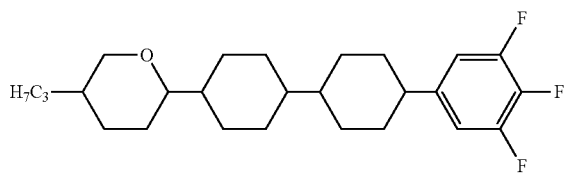

or

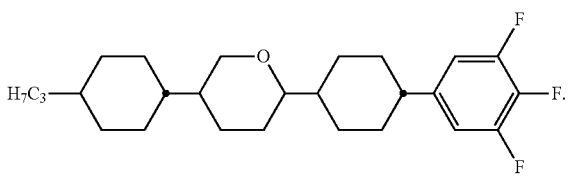

17. A compound according to claim 1, which is a compound of the following formula

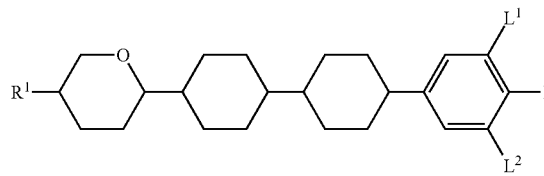

wherein

| R¹ | X¹ | L¹ | L² |
|---|---|---|---|
| H | F | H | H |
| CH₃ | F | H | H |
| C₂H₅ | F | H | H |
| n-C₃H₇ | F | H | H |
| n-C₄H₉ | F | H | H |
| n-C₅H₁₁ | F | H | H |
| n-C₆H₁₃ | F | H | H |
| H | F | F | H |
| CH₃ | F | F | H |
| C₂H₅ | F | F | H |
| n-C₃H₇ | F | F | H |
| n-C₄H₉ | F | F | H |
| n-C₅H₁₁ | F | F | H |
| n-C₆H₁₃ | F | F | H |
| H | F | F | F |
| CH₃ | F | F | F |
| C₂H₅ | F | F | F |
| n-C₃H₇ | F | F | F |
| nC₄H₉ | F | F | F |
| n-C₅H₁₁ | F | F | F |
| n-C₆H₁₃ | F | F | F |
| H | OCF₃ | H | H |
| CH₃ | OCF₃ | H | H |
| C₂H₅ | OCF₃ | H | H |
| n-C₃H₇ | OCF₃ | H | H |
| n-C₄H₉ | OCF₃ | H | H |
| n-C₅H₁₁ | OCF₃ | H | H |
| n-C₆H₁₃ | OCF₃ | H | H |
| H | OCF₃ | F | H |
| CH₃ | OCF₃ | F | H |
| C₂H₅ | OCF₃ | F | H |
| n-C₃H₇ | OCF₃ | F | H |
| n-C₄H₉ | OCF₃ | F | H |
| n-C₅H₁₁ | OCF₃ | F | H |
| n-C₆H₁₃ | OCF₃ | F | H |
| H | OCF₃ | F | F |
| CH₃ | OCF₃ | F | F |
| C₂H₅ | OCF₃ | F | F |
| n-C₃H₇ | OCF₃ | F | F |
| nC₄H₉ | OCF₃ | F | F |
| n-C₅H₁₁ | OCF₃ | F | F |
| n-C₆H₁₃ | OCF₃ | F | F |
| H | CN | H | H |
| CH₃ | CN | H | H |
| C₂H₅ | CN | H | H |
| n-C₃H₇ | CN | H | H |
| n-C₄H₉ | CN | H | H |
| n-C₅H₁₁ | CN | H | H |
| n-C₆H₁₃ | CN | H | H |
| H | CN | F | H |
| CH₃ | CN | F | H |
| C₂H₅ | CN | F | H |
| n-C₃H₇ | CN | F | H |
| n-C₄H₉ | CN | F | H |
| n-C₅H₁₁ | CN | F | H |
| n-C₆H₁₃ | CN | F | H |
| H | CN | F | F |
| CH₃ | CN | F | F |
| C₂H₅ | CN | F | F |
| n-C₃H₇ | CN | F | F |
| nC₄H₉ | CN | F | F |
| n-C₅H₁₁ | CN | F | F |
| n-C₆H₁₃ | CN | F | F |
| H | OCHF₂ | H | H |
| CH₃ | OCHF₂ | H | H |
| C₂H₅ | OCHF₂ | H | H |
| n-C₃H₇ | OCHF₂ | H | H |
| n-C₄H₉ | OCHF₂ | H | H |
| n-C₅H₁₁ | OCHF₂ | H | H |
| n-C₆H₁₃ | OCHF₂ | H | H |
| H | OCHF₂ | F | H |
| CH₃ | OCHF₂ | F | H |
| C₂H₅ | OCHF₂ | F | H |
| n-C₃H₇ | OCHF₂ | F | H |
| n-C₄H₉ | OCHF₂ | F | H |
| n-C₅H₁₁ | OCHF₂ | F | H |
| n-C₆H₁₃ | OCHF₂ | F | H |
| H | OCHF₂ | F | F |
| CH₃ | OCHF₂ | F | F |
| C₂H₅ | OCHF₂ | F | F |
| n-C₃H₇ | OCHF₂ | F | F |
| nC₄H₉ | OCHF₂ | F | F |
| n-C₅H₁₁ | OCHF₂ | F | F |
| n-C₆H₁₃ | OCHF₂ | F | F |
| H | CF₃ | H | H |
| CH₃ | CF₃ | H | H |
| C₂H₅ | CF₃ | H | H |
| n-C₃H₇ | CF₃ | H | H |
| n-C₄H₉ | CF₃ | H | H |
| n-C₅H₁₁ | CF₃ | H | H |
| n-C₆H₁₃ | CF₃ | H | H |
| H | CF₃ | F | H |
| CH₃ | CF₃ | F | H |
| C₂H₅ | CF₃ | F | H |
| n-C₃H₇ | CF₃ | F | H |
| n-C₄H₉ | CF₃ | F | H |
| n-C₅H₁₁ | CF₃ | F | H |
| n-C₆H₁₃ | CF₃ | F | H |
| H | CF₃ | F | F |
| CH₃ | CF₃ | F | F |
| C₂H₅ | CF₃ | F | F |
| n-C₃H₇ | CF₃ | F | F |
| nC₄H₉ | CF₃ | F | F |
| n-C₅H₁₁ | CF₃ | F | F |
| n-C₆H₁₃ | CF₃ | F | F |
| H | CH₃ | F | F |
| CH₃ | CH₃ | F | F |
| C₂H₅ | CH₃ | F | F |
| n-C₃H₇ | CH₃ | F | F |
| nC₄H₉ | CH₃ | F | F |
| n-C₅H₁₁ | CH₃ | F | F |
| n-C₆H₁₃ | CH₃ | F | F |
| H | CH₃ | F | H |
| CH₃ | CH₃ | F | H |
| C₂H₅ | CH₃ | F | H |
| n-C₃H₇ | CH₃ | F | H |
| nC₄H₉ | CH₃ | F | H |
| n-C₅H₁₁ | CH₃ | F | H |
| n-C₆H₁₃ | CH₃ | F | H |
| H | CH₃ | H | H |
| CH₃ | CH₃ | H | H |
| C₂H₅ | CH₃ | H | H |
| n-C₃H₇ | CH₃ | H | H |
| nC₄H₉ | CH₃ | H | H |
| n-C₅H₁₁ | CH₃ | H | H or |
| n-C₆H₁₃ | CH₃ | H | H | or a compound of the following formula

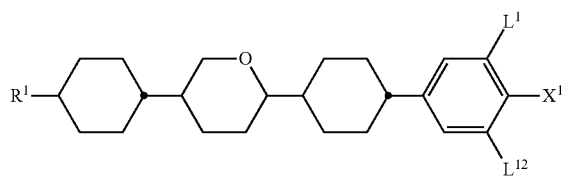

where

| R¹ | X¹ | L¹ | L² |
|---|---|---|---|
| H | F | H | H |
| CH₃ | F | H | H |
| C₂H₅ | F | H | H |
| n-C₃H₇ | F | H | H |
| n-C₄H₉ | F | H | H |
| n-C₅H₁₁ | F | H | H |
| n-C₆H₁₃ | F | H | H |
| H | F | F | H |
| CH₃ | F | F | H |
| C₂H₅ | F | F | H |
| n-C₃H₇ | F | F | H |
| n-C₄H₉ | F | F | H |
| n-C₅H₁₁ | F | F | H |
| n-C₆H₁₃ | F | F | H |
| H | F | F | F |
| CH₃ | F | F | F |
| C₂H₅ | F | F | F |
| n-C₃H₇ | F | F | F |
| nC₄H₉ | F | F | F |
| n-C₅H₁₁ | F | F | F |
| n-C₆H₁₃ | F | F | F |
| H | OCF₃ | H | H |
| CH₃ | OCF₃ | H | H |
| C₂H₅ | OCF₃ | H | H |
| n-C₃H₇ | OCF₃ | H | H |
| n-C₄H₉ | OCF₃ | H | H |
| n-C₅H₁₁ | OCF₃ | H | H |
| n-C₆H₁₃ | OCF₃ | H | H |
| H | OCF₃ | F | H |
| CH₃ | OCF₃ | F | H |
| C₂H₅ | OCF₃ | F | H |
| n-C₃H₇ | OCF₃ | F | H |
| n-C₄H₉ | OCF₃ | F | H |
| n-C₅H₁₁ | OCF₃ | F | H |
| n-C₆H₁₃ | OCF₃ | F | H |
| H | OCF₃ | F | F |
| CH₃ | OCF₃ | F | F |
| C₂H₅ | OCF₃ | F | F |
| n-C₃H₇ | OCF₃ | F | F |
| nC₄H₉ | OCF₃ | F | F |
| n-C₅H₁₁ | OCF₃ | F | F |
| n-C₆H₁₃ | OCF₃ | F | F |
| H | CN | H | H |
| CH₃ | CN | H | H |
| C₂H₅ | CN | H | H |
| n-C₃H₇ | CN | H | H |
| n-C₄H₉ | CN | H | H |
| n-C₅H₁₁ | CN | H | H |
| n-C₆H₁₃ | CN | H | H |
| H | CN | F | H |
| CH₃ | CN | F | H |
| C₂H₅ | CN | F | H |
| n-C₃H₇ | CN | F | H |
| n-C₄H₉ | CN | F | H |
| n-C₅H₁₁ | CN | F | H |
| n-C₆H₁₃ | CN | F | H |
| H | CN | F | F |
| CH₃ | CN | F | F |
| C₂H₅ | CN | F | F |
| n-C₃H₇ | CN | F | F |
| nC₄H₉ | CN | F | F |
| n-C₅H₁₁ | CN | F | F |
| n-C₆H₁₃ | CN | F | F |
| H | OCHF₂ | H | H |
| CH₃ | OCHF₂ | H | H |
| C₂H₅ | OCHF₂ | H | H |
| n-C₃H₇ | OCHF₂ | H | H |
| n-C₄H₉ | OCHF₂ | H | H |
| n-C₅H₁₁ | OCHF₂ | H | H |
| n-C₆H₁₃ | OCHF₂ | H | H |
| H | OCHF₂ | F | H |
| CH₃ | OCHF₂ | F | H |
| C₂H₅ | OCHF₂ | F | H |
| n-C₃H₇ | OCHF₂ | F | H |
| n-C₄H₉ | OCHF₂ | F | H |
| n-C₅H₁₁ | OCHF₂ | F | H |
| n-C₆H₁₃ | OCHF₂ | F | H |
| H | OCHF₂ | F | F |
| CH₃ | OCHF₂ | F | F |
| C₂H₅ | OCHF₂ | F | F |
| n-C₃H₇ | OCHF₂ | F | F |
| nC₄H₉ | OCHF₂ | F | F |
| n-C₅H₁₁ | OCHF₂ | F | F |
| n-C₆H₁₃ | OCHF₂ | F | F |
| H | CF₃ | H | H |
| CH₃ | CF₃ | H | H |
| C₂H₅ | CF₃ | H | H |
| n-C₃H₇ | CF₃ | H | H |
| n-C₄H₉ | CF₃ | H | H |
| n-C₅H₁₁ | CF₃ | H | H |
| n-C₆H₁₃ | CF₃ | H | H |
| H | CF₃ | F | H |
| CH₃ | CF₃ | F | H |
| C₂H₅ | CF₃ | F | H |
| n-C₃H₇ | CF₃ | F | H |
| n-C₄H₉ | CF₃ | F | H |
| n-C₅H₁₁ | CF₃ | F | H |
| n-C₆H₁₃ | CF₃ | F | H |
| H | CF₃ | F | F |
| CH₃ | CF₃ | F | F |
| C₂H₅ | CF₃ | F | F |
| n-C₃H₇ | CF₃ | F | F |
| nC₄H₉ | CF₃ | F | F |
| n-C₅H₁₁ | CF₃ | F | F or |
| n-C₆H₁₃ | CF₃ | F | F. |

18. A compound according to claim 1, wherein n denotes 2.

19. A compound according to claim 1, wherein n denotes 3.

\* \* \* \* \*

UNITED STATES PATENT AND TRADEMARK OFFICE
CERTIFICATE OF CORRECTION

PATENT NO. : 8,465,672 B2  
APPLICATION NO. : 12/377820  
DATED : June 18, 2013  
INVENTOR(S) : Lietzau et al.

Page 1 of 1

It is certified that error appears in the above-identified patent and that said Letters Patent is hereby corrected as shown below:

On the Title Page, Item (22) reads "Jul. 17, 2007" should read -- Jul. 19, 2007 --

In the Claims

Column 32, line 7 reads "n-$C_5H_{11}$ $OCHF_7$ H H" should read -- n-$C_5H_{11}$ $OCHF_2$ H H --

Column 32, line 8 reads "n-$C_6H_{13}$ $OCHF_7$ H H" should read -- n-$C_6H_{13}$ $OCHF_2$ H H --

Signed and Sealed this  
First Day of October, 2013

Teresa Stanek Rea  
*Deputy Director of the United States Patent and Trademark Office*